(12) United States Patent
Marmaropoulos et al.

(10) Patent No.: US 6,718,200 B2
(45) Date of Patent: Apr. 6, 2004

(54) WEARABLE BODY-FAT SENSOR

(75) Inventors: George Marmaropoulos, Yorktown Heights, NY (US); Clive van Heerden, London (GB); Giang Vu, Ossining, NY (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 140 days.

(21) Appl. No.: 10/116,549

(22) Filed: Apr. 4, 2002

(65) Prior Publication Data

US 2002/0169387 A1 Nov. 14, 2002

Related U.S. Application Data

(60) Provisional application No. 60/282,887, filed on Apr. 10, 2001.

(51) Int. Cl.$^7$ ................................................. A61B 5/05
(52) U.S. Cl. ..................................................... 600/547
(58) Field of Search .............................. 600/547, 587, 600/506, 507; 2/1, 69; 73/433; 177/4, 5, 245; 128/897, 898, 920

(56) References Cited

U.S. PATENT DOCUMENTS 5,449,000 A * 9/1995 Libke et al. ................ 600/547
6,188,925 B1 * 2/2001 Kawanishi et al. .......... 600/547
6,292,690 B1 9/2001 Petrucelli et al. ........... 600/547
6,370,425 B1 * 4/2002 Oguma ....................... 600/547

FOREIGN PATENT DOCUMENTS

| JP | 11128199 A | * | 5/1999 | ............ A61B/5/05 |
| JP | 2000014655 A | * | 1/2000 | ............ A61B/5/05 |
| JP | 2000237159 A | * | 9/2000 | ............ A61B/5/05 |

* cited by examiner

Primary Examiner—Charles Marmor (57) ABSTRACT

A wearable garment having an electrode and sensors mounted in a predetermined position relative to the wearer's skin provides a quick and efficient way to measure the body-fat composition of the person. The body-fat sensor includes a pair of shoes having a weight-measuring sensor and a wearable body structure, of flexible material, having an inner surface, wherein a flexible electrical conductor is affixed to the inner surface of the wearable body structure. The body-fat sensor further includes an impedance-measuring circuit having at least one pair of electrodes, where the pair of electrodes is electrically coupled to both ends of the electrical conductor, so that the body-fat composition of the person can be measured based on the data received from the weight sensor and the impedance-measuring circuit.

21 Claims, 7 Drawing Sheets

WEARABLE BODY-FAT SENSOR

CROSS REFERENCE TO RELATED APPLICATION

This application claims the benefit of U.S. Provisional Application Ser. No. 60/282,887, filed Apr. 10, 2001, the teachings of which are incorporated herein by reference.

BACKGROUND OF THE INVENTION

1. Field of the Invention

The present invention relates to equipment used in the monitoring of human body fat and, in particular, to a wearable body-fat sensor using impedance pulses to obtain the body-fat level by contact with the surface of a wearer's skin.

2. Description of the Related Art

Increased amounts of fat in the human body have been associated with increased risks of serious medical complications, including cardiovascular problems, diabetes, and other adult diseases. In consideration of health risks from obesity a number of instruments are commercially available to estimate the composition of body fat. Most prior art devices have disadvantages in that the person has to input other parameters, such as weight, height, age, and sex, through an input interface during each reading. Further, they give inconvenience to the users who are not familiar with the operation of the measuring devices.

Accordingly, the present invention provides an improved body-fat sensor that is easy to use and that estimates the body-fat composition by allowing the sensor to be conveniently attached to the inner surface of a wearable garment, such as a shirt, shoes or socks.

SUMMARY OF THE INVENTION

The present invention relates to a method and apparatus for detecting a body fat composition that may be implemented in hardware, in software, or in a combination of hardware and software as desired for a particular application, such that the detection can be realized in a simple, efficient, and reliable implementation.

According to one aspect of the invention, an apparatus for detecting the body-fat composition of a person includes a wearable body structure, of flexible material, having an inner surface; a flexible electrical conductor affixed to the inner surface, the conductor having a first-end portion and a second-end portion; an electronic circuit having at least one pair of electrodes electrically and mechanically affixed to the inner surface of the wearable body structure, the pairs of electrodes being electrically coupled to the first end of the electrical conductor and the second end of the electrical conductor; a weight sensor for measuring the weight of the person; and, the electronic circuit operative to determine the body-fat composition based on the impedance measured across the pairs of electrodes, the weight of the person, and a predetermined data, which includes height age, and sex of the person.

According to another aspect of the invention, an apparatus for detecting a body-fat composition of a person includes: a pair of shoes having a weight sensor; a wearable body structure, of flexible material, having an inner surface; a flexible electrical conductor affixed to the inner surface, the conductor having a first-end portion and a second-end portion; an impedance-measuring circuit having at least one pair of electrodes, the pairs of electrodes being electrically coupled to the first end of the electrical conductor and the second end of the electrical conductor; a memory for storing data, which includes height, age, and sex of the person; and, a controller for processing data received from the weight sensor, the impedance-measuring circuit, and the memory to determine the body-fat composition of the person.

According to the preferred embodiment of this invention, the electrical conductor is integrated into the flexible material of the body structure in the form of fibers of conductive material supported by fibers of substantially non-conductive material. In addition, the electrical conductor may be printed on the inner surface of the wearable body structure in the form of electrically-conductive coating material. The preferred apparatus further includes a display for displaying the body-fat composition of the person, a power source for providing an electrical flow between the pair of electrodes, and at least one pair of shoes containing the weight sensor. At least one pair of electrodes is provided in the shoes for contact with a right sole and a left sole in order to measure the impedance according to a voltage difference between the pair of electrodes. The electrodes may be also formed to contact a right palm and a left palm when the person wears the wearable body structure as well as a right ankle and a left ankle when the person wears the wearable body structure.

According to a further aspect of the invention, a method for measuring the body-fat composition of a person includes the steps of: (a) inputting height, sex, and age of the person to a controller; (b) standing on a pair of shoes having a weight-measuring sensor to measure the weight of the person and to contact a right sole and a left sole on a pair of electrodes; (c) providing an electrical path between the pairs of electrodes; (d) detecting a voltage difference between the pair of electrodes to measure an impedance by means of an impedance-measuring circuit; and, (e) calculating a body-fat percentage by means of the controller. The method further includes the step of wearing a garment structure having a flexible electrical conductor coupled to a second pair of electrodes at both ends thereof, thereby making contact with a right wrist and a left wrist on the second pair of electrodes and repeating steps (c) through (e).

The foregoing and other features and advantages of the invention will be apparent from the following, more detailed description of preferred embodiments as illustrated in the accompanying drawings in which reference characters refer to the same parts throughout the various views. The drawings are not necessarily to scale, the emphasis instead is placed upon illustrating the principles of the invention.

DETAILED DESCRIPTION OF THE PREFERRED EMBODIMENT

In the following description, for purposes of explanation rather than limitation, specific details are set forth such as the particular architecture, interfaces, techniques, etc., in order to provide a thorough understanding of the present invention. However, it will be apparent to those skilled in the art that the present invention may be practiced in other embodiments, which depart from these specific details. For purposes of simplicity and clarity, detailed descriptions of well-known devices, circuits, and methods are omitted so as not to obscure the description of the present invention with unnecessary detail.

Figure 1:
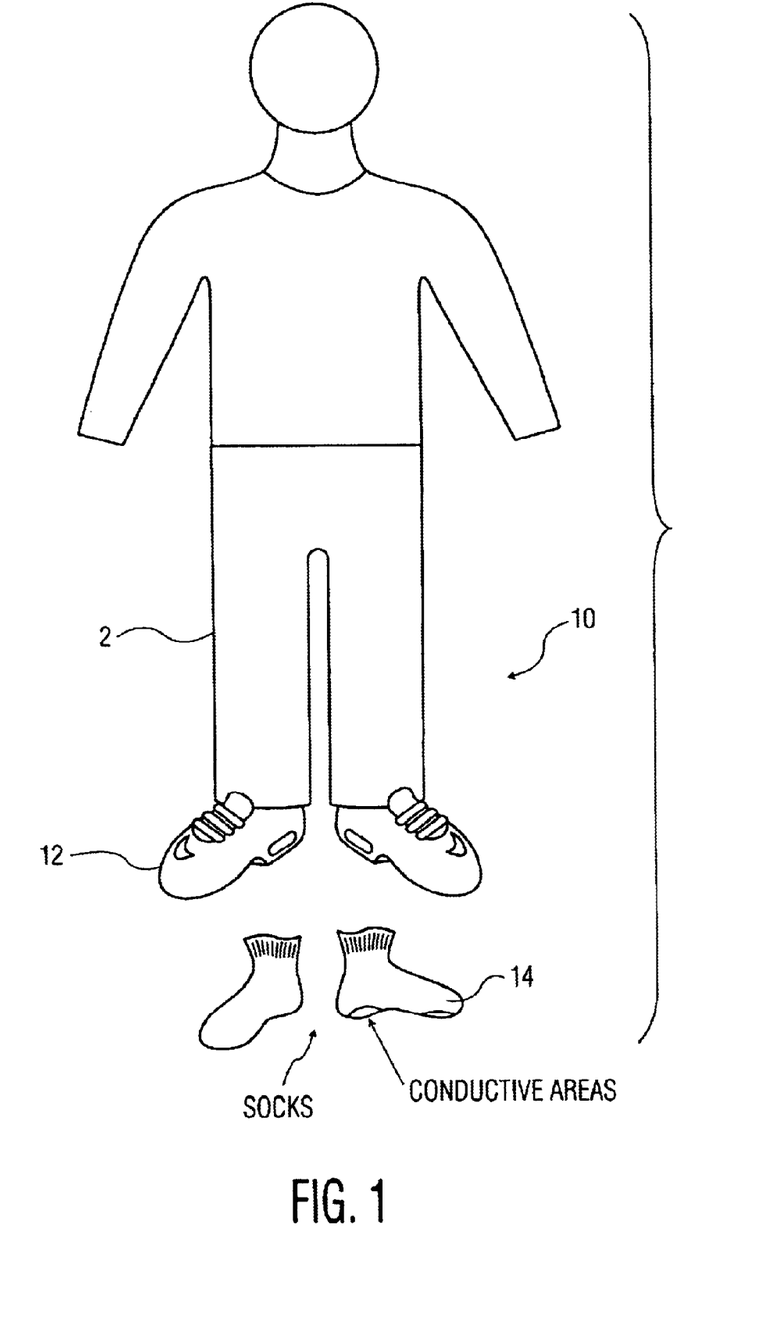
FIG. 1 is simplified pictorial representation of a wearable body sensor of the type used in accordance with this invention.

FIG. 1 illustrates a simplified pictorial representation whereto the embodiment of the present invention is applicable. The wearable body-fat-sensor system 10 constructed in accordance with this invention includes the necessary electronics and display in the shoes 12 or is integrated into the garment 2. According to the embodiment of the present invention, at least one pair of electrodes is integrated on the insole of each shoe 12 or in the garment 2, so that the electric current flows from the electrode on one body limb to the electrode on the other body limb to detect the impedance of the body. Specifically, an alternating current flow between the electrodes is controlled to obtain the voltage difference, so that the impedance of the user's body can be measured. The electronic circuit, embedded in the shoes 12 or the garment 2, will then calculate the body-fat composition using the Bioelectrical-Impedance-Analysis (BIA) method as well as other parameters given in advance by the user, such as weight height, age, and sex. In the preferred embodiment, a weighing device can be integrated in the shoes 12.

It should be noted that calculating body-fat composition is well known in the art and can be performed in a variety of ways. In particular, the Bioelectrical-Impedance Analysis (BIA) is one of the widely-used methods that is simple, quick, and noninvasive for screening body fat. See for example, U.S. Pat. No. 6,292,690 issued on Sep. 18, 2001, the content of which is hereby incorporated by reference. This method is based on the fact that when an electrical signal passes through the body, the impedance to this signal is affected by the amount of fluid in the body. Taking into account other parameters such as height, weight, sex, and age, the mass of body fat can be estimated using the BIA algorithm.

In the case of measuring the impedance by means of shoes 12, the user wears the shoes 12 either with no socks or with special socks 14 that utilize conductive fibers in the area where the surface of the socks touches the surface of the shoe insole, thereby allowing good electrical conductivity between the skin and the electrodes. The soles of the shoes 12, formed by a conductive fabric are secured to the user's feet and further include an electronic circuit located within the body of the shoes in a predetermined location to automatically measure the weight and calculate the body-fat composition. To this end, an electrical connection is required between the shoes 12 by means of a conductive cord or other conductive material to combine data from one shoe to the other.

Figure 2:
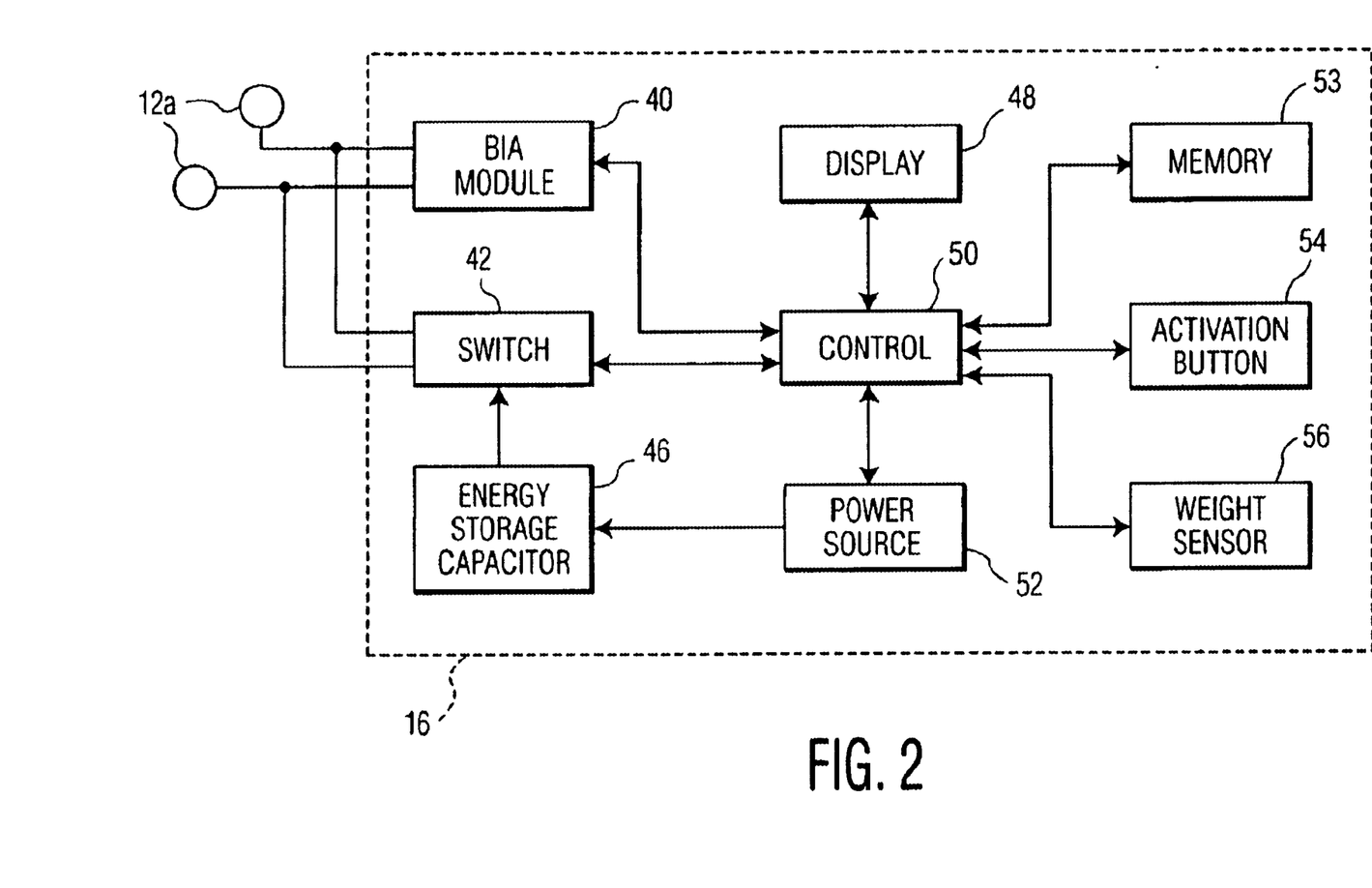
FIG. 2 is a block diagram illustrating the architecture of the wearable body-sensor system in accordance with this invention.

FIG. 2 depicts a representative hardware of the electronic circuit 16 capable of measuring the body-fat composition according to the present invention. As shown in FIG. 2, the circuit 16, which may be mounted to the inner or outer surface of the shoes 12, may be seen to comprise at least one pair of electrodes 12a; a BIA module 40; a switch 42; an energy-storage capacitor 46; a display 48; a controller 50; a power source 52; a memory 53; an activation button 54; and, a weight sensor 56. The electrodes 12a are located in a predetermined location in the shoes 12 selected to place the electrodes substantially in contact relationship at a desired surface location on the foot of a person (i.e., a front sole or a rear sole) or the skin of the person. The BIA module 40 is connected to the electrodes 12a to amplify, filter, and digitize (using an analog to a digital converter) an electrical-impedance signal generated from the person's body by measuring the impedance across the electrodes 12a. The detected impedance-sample signals are provided to the controller 50, which runs a bioelectrical-impedance algorithm (See U.S. Pat. No. 6,292,690 cited earlier) for detecting body-fat composition. As the electrodes 12a are placed directly under the surface of the foot, the ability to detect impedance can be improved compared to the prior art system because there is no need to attach the electrodes to the hands and feet. Moreover, the inconvenience of inputting the sex, age, weight, and height of the measuring person during each operation is eliminated in accordance with the techniques of the present invention as this information is pre-recorded in the memory 53.

The display 48, connected to the controller 50, is preferably a liquid-crystal display (LCD) and provides audio and visible feedback to the user. In the embodiment, the display 48 may be integrated in the shoes 12 or the garment 2. The activation button 54, which may have both automatic and manual modes, is connected to the controller 50 to enable the user to selectively activate the measurement of body-fat composition. The power source 52 provides power to the circuit 16 and in particular to the energy-storage capacitor 46, which charges a lower-level current between the electrodes 12a via the switch 42 to measure the impedance of the wearer's body. It will be apparent to those skilled in the art that a variety of RC arrangements can be implemented to generate the desired voltage levels. Note that various hardware configurations readily apparent to those skilled in the art can be used for the circuit 16. Alternatively, the function of the circuit 16 can be performed by functionally-equivalent circuits, such as a digital-processor circuit or an application-specific-integrated circuit (ASIC).

Figure 3:
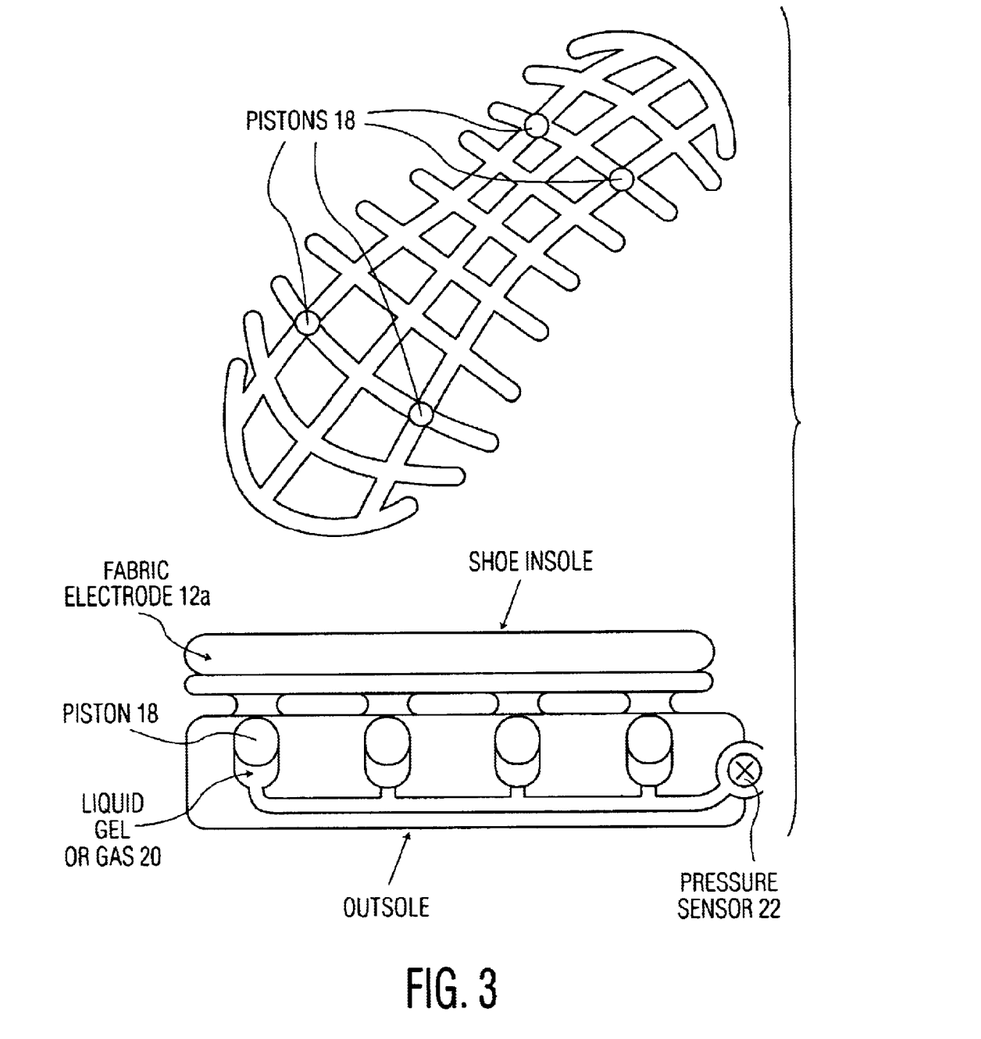
FIG. 3 is a simplified pictorial representation of a portion of the shoes of FIG. 1, constructed in accordance with this invention.

Referring to FIG. 2, the weight information can be given to the circuit 16 automatically by using the weighing sensor 56 integrated in the shoes 12 according to the preferred embodiment of the present invention. As shown in FIG. 3, the fabric electrodes 12a must be electrically conductive to satisfy the well-known electrical-operating requirements of electrode-contact sensors. The weight force is transformed to the surface pressure applied on a number of pistons 18 distributed between the insole and outsole of the shoes 12. The pressure is then applied to a liquid, gel, or gas 20 inside a network of chambers. A pressure sensor 22 measures the pressure of the liquid, gel, or gas 20 and calculates the weight based on the known piston surface. Data from one shoe is combined with data from the other. If the circuit 16 is integrated in the garment 2, the weight information can be transmitted to the circuit 16 of the garment in a conventional manner of data transfer known to those skilled in this art. As such, the user can monitor the body-fat composition on a continuing basis by simply wearing the shoes 12. Note that the body-fat percentage may vary over a time period but not one's shoe size. Thus, the present invention provides a subsequent reading of one's body-fat percentage without the tedious requirement of inputting all the necessary information again.

Figure 4:
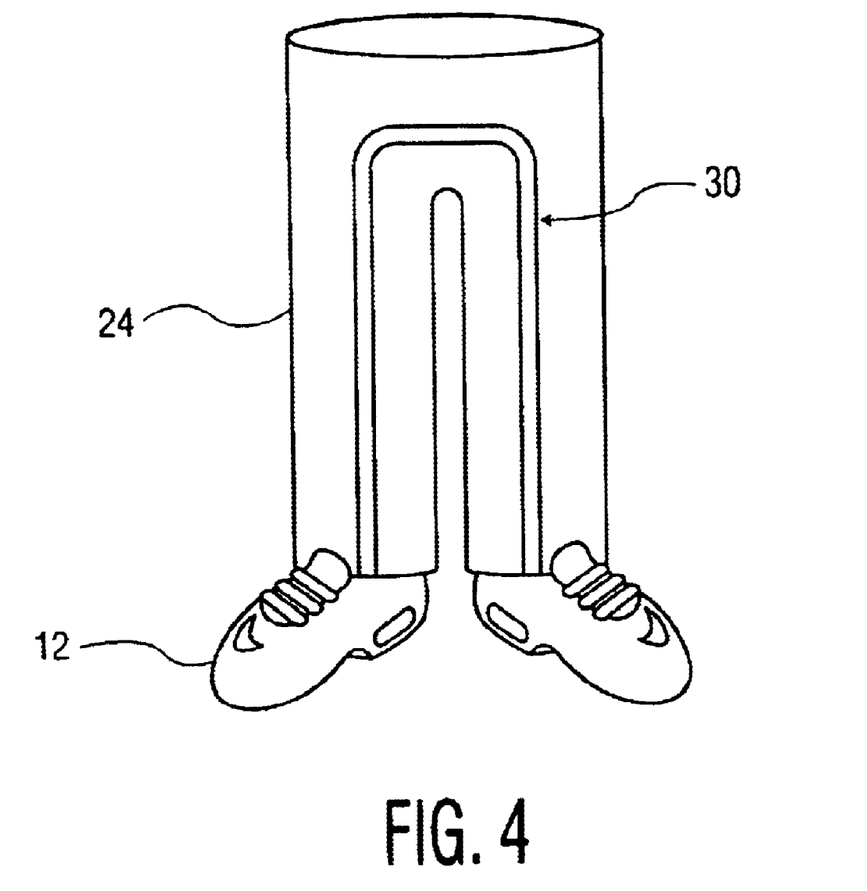
FIG. 4 is a simplified pictorial representation of a wearable body sensor of the type in accordance with another embodiment of this invention.

FIG. 4 illustrates a wearable body-fat-sensor system 10 according to a second embodiment of the present invention. The construction and operation of the second embodiment are essentially the same as those described above with respect to FIGS. 1 and 2, except that the electrodes 12a are electrically coupled to a conductive track 30 and are integrated into the trouser 24. Hence, the discussion of similar components described in the preceding paragraphs is omitted to avoid redundancy, as they are described with respect to FIG. 2. Again, the circuit 16 may be integrated in the shoes 12 or in the trouser 24 in the second embodiment. In the preferred form here disclosed, the conductive track 30 is formed by conductive materials, such as a concealed wire, printed conductive ink on textiles/fabrics, and conductive fibers and embroidery, so that they are electrically conductive to satisfy the well-known electrical-operating requirements of electrode-contact sensors. Flexibility is a particularly desirable characteristic of the conductive track 30 for use in this invention as it avoids the possibility of undesirable chafing and skin abrasion which would be likely to result from engaging a living skin tissue with the hard edge of a rigid contact/sensor structure. For the purposes of this invention, a durable, cleanable plastic material is preferred with the added requirement that the plastic must be electrically conductive. Plastic materials meeting the requirements of durability, cleanability and electrical conductivity are well-known and widely available. To avoid confusion and prolixity, the nature and structure of these materials are not discussed or described further in this disclosure.

It will now be apparent to those with a reasonable skill in this art, that the wearable body-fat-sensor system 10 constructed in accordance with the second embodiment of this invention will provide contact sensors positioned on the inner surface of a wearable trouser 24 in a predetermined position to contact a desired location on the wearer's skin. In particular, the impedance from the right ankle to the joint of the right-hip area and from the left ankle to the joint of the left-hip area can be measured based on a voltage-current ratio by making a current flow between the electrodes 12a and the conductive track 30, then the measured impedance can be used to measure a more accurate body-fat percentage of the wearer's body.

Figure 5:
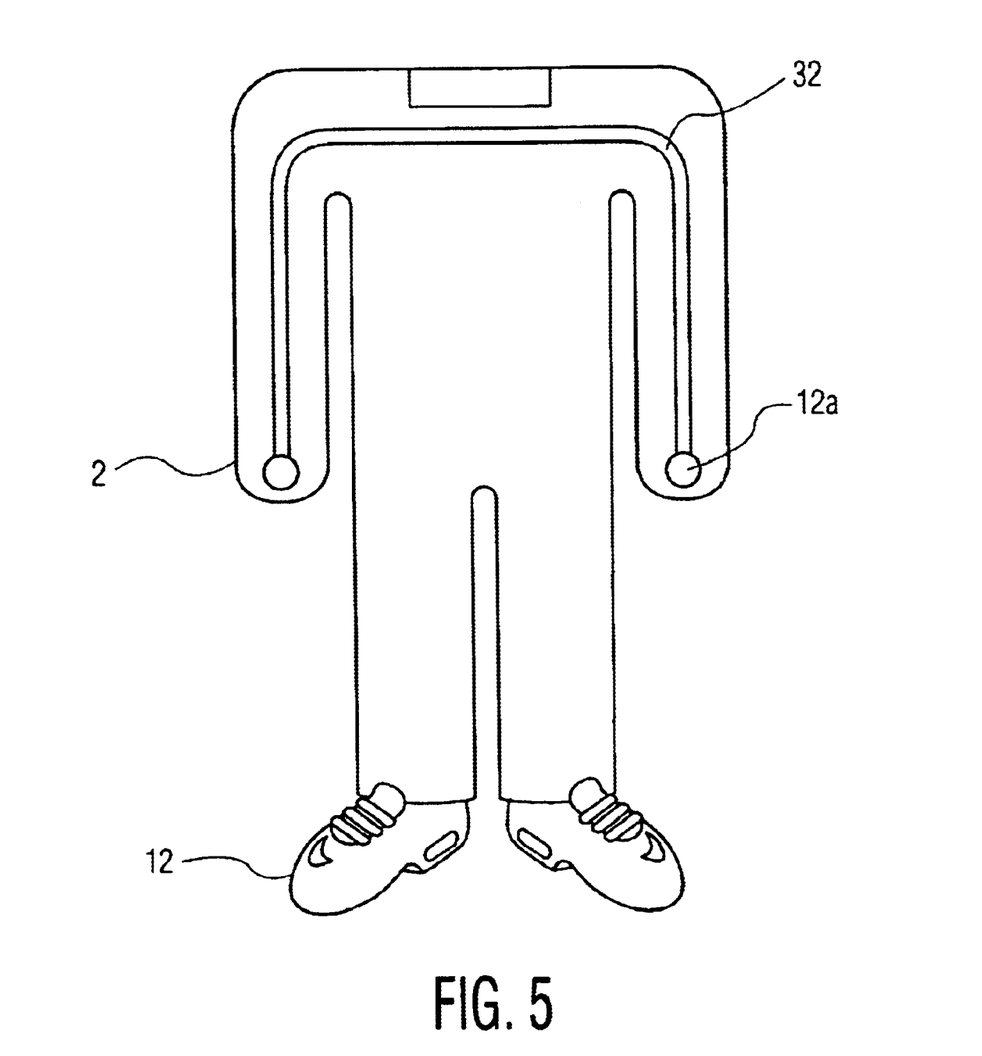
FIG. 5 is a simplified pictorial representation of a wearable body sensor of the type in accordance with yet another embodiment of this invention.

FIG. 5 illustrates a wearable body-fat-sensor system 10 according to a third embodiment of the present invention. The construction and operation of the third embodiment are essentially the same as those described above with respect to FIG. 4. The only notable difference is that a conductive track 32 is provided between the electrodes 12a from the left wrist extending through the shoulder area and to the right wrist. Thus, the discussion of similar components described in the preceding paragraphs is omitted to avoid redundancy. As shown in FIG. 5, the impedance from the left wrist to the joint of the left-shoulder area and from the right wrist to the joint of the right-shoulder area are measured, so that the voltage between the electrodes 12a can be measured. Thereafter, the measured impedance is analyzed and undergoes the bioelectrical-impedance algorithm to determine the body-fat percent of the person based on the measured impedance, weight, height, and sex.

Figure 6:
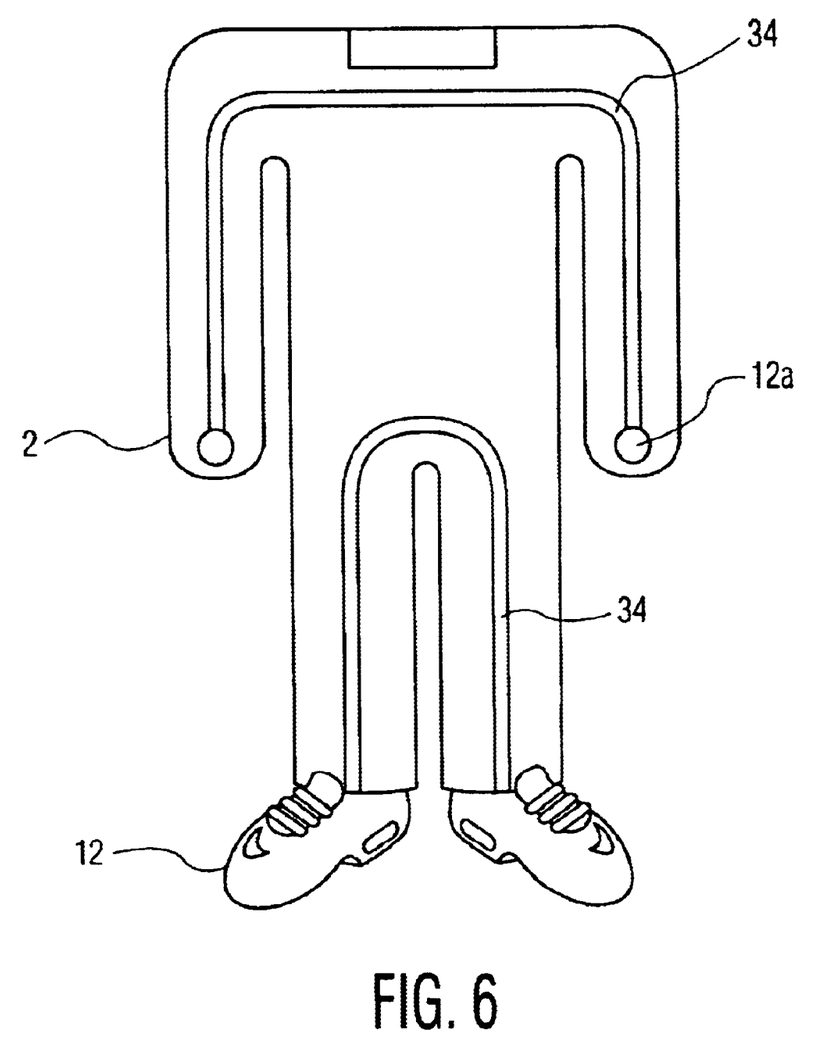
FIG. 6 is a simplified pictorial representation of a wearable body sensor of the type in accordance with another embodiment of this invention; and, FIG. 7 is a simplified pictorial representation of a wearable body sensor of the type in accordance with another embodiment of this invention.

FIG. 6 illustrates a wearable body-fat-sensor system 10 according to a fourth embodiment of the present invention. Again, the construction and operation of the fourth embodiment are essentially the same as those described above with respect to FIGS. 4 and 5. Here, the conductive track 34 is provided to measure impedance from the left wrist to the right wrist and from the left ankle to the right ankle, as shown in FIG. 6. Hence, the discussion of similar components described in the preceding paragraphs is omitted to avoid redundancy, as they are described with respect to FIGS. 4 and 5. The measured impedances through the conductive track 34 are analyzed, then the body-fat composition of the person can be obtained using the bioelectrical-impedance algorithm described earlier.

Figure 7:
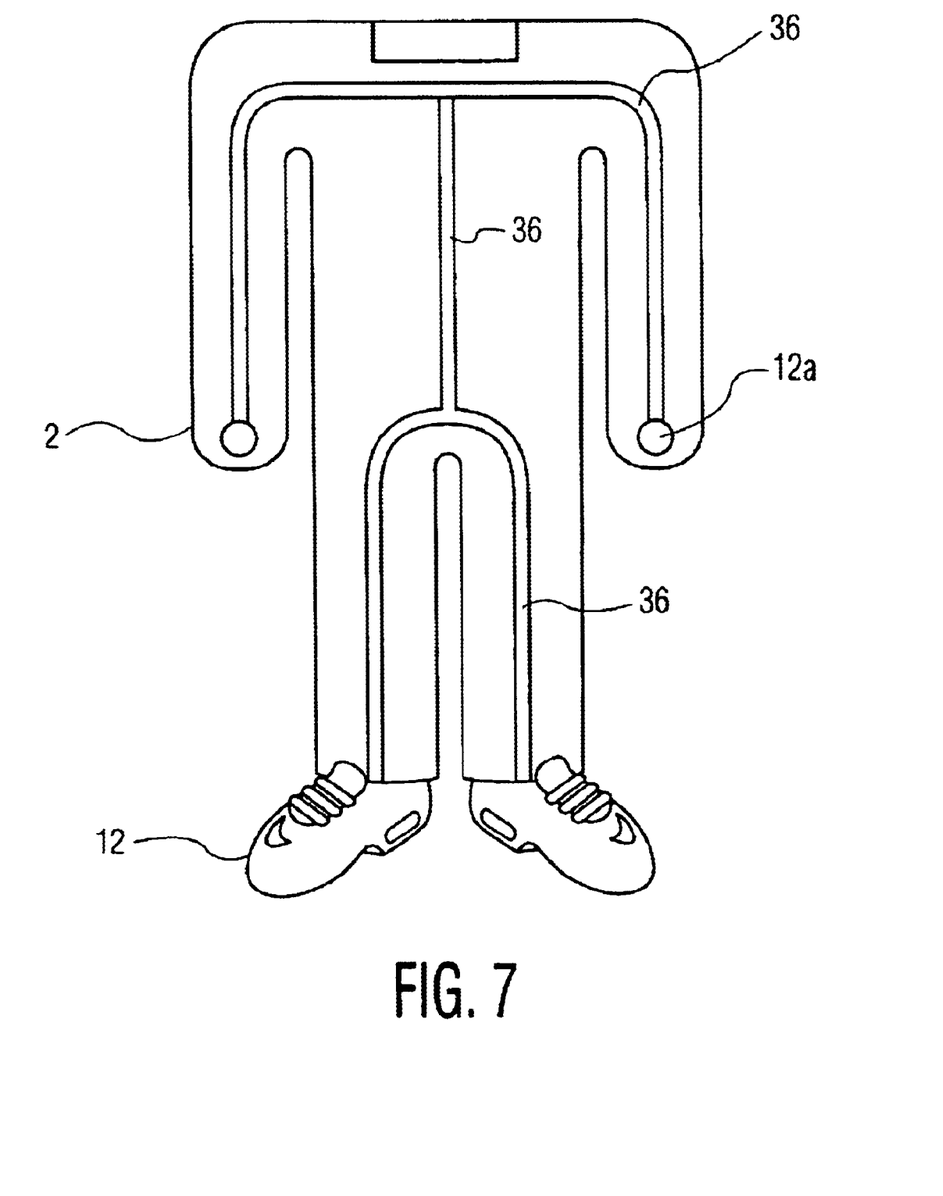

FIG. 7 illustrates a wearable body-fat-sensor system 10 according to a fifth embodiment of the present invention. The discussion of similar components is omitted to avoid redundancy, as they are described in FIGS. 4 through 6. As shown in FIG. 7, the impedance is measured from the left wrist to the right wrist, from the left ankle to the right ankle, and from the upper-chest area to the lower-stomach area by means of a conductive track 36. Based on the measured impedances, the body composition such as the body-fat proportion is analyzed.

Having thus described the preferred embodiment of an apparatus and method for detecting the body-fat composition of a person using a wearable body-fat sensor, it should be apparent to those skilled in the art that certain advantages of the present invention have been achieved. The foregoing is to be constructed as being only an illustrative embodiment of this invention. Persons skilled in the art can easily conceive of alternative arrangements providing a functionality similar to this embodiment without any deviation from the fundamental principles or the scope of this invention. Therefore, it is intended that the present invention not be limited to the particular embodiment disclosed as the best mode contemplated for carrying out the present invention, but that the present invention include all embodiments falling within the scope of the appended claims.

What is claimed is:

1. An apparatus for detecting the body-fat composition of a person, comprising:
    a wearable body structure, of flexible material, having an inner surface;
    a flexible electrical conductor affixed to said inner surface, said conductor having a first-end portion and a second-end portion;
    an electronic circuit having at least one pair of electrodes electrically and mechanically affixed to said inner surface of said wearable body structure, said pairs of electrodes being electrically coupled to said first end of said electrical conductor and said second end of said electrical conductor;
    a weight sensor for measuring the weight of said person; and,
    said electronic circuit operative to determine the body-fat composition based on the impedance measured across said pairs of electrodes, the weight of said person, and a predetermined data relating to said person.

2. The apparatus of claim 1, wherein said electrical conductor is integrated into the flexible material of said wearable body structure in the form of fibers of conductive material supported by fibers of substantially non-conductive material.

3. The apparatus of claim 1, wherein said electrical conductor is printed on said inner surface of said wearable body structure in the form of electrically-conductive coating material.

4. The apparatus of claim 1, further comprising a display for displaying the body-fat composition of said person.

5. The apparatus of claim 1, further comprising a power source for providing an electrical flow between said pair of electrodes.

6. The apparatus of claim 1, further comprising at least one pair of shoes containing said weight sensor therein.

7. The apparatus of claim 5, wherein said pair of electrodes is provided in said shoes for contact with a right sole and a left sole for measuring the impedance based on a voltage difference between said pair of electrodes.

8. The apparatus of claim 1, wherein said pair of electrodes is formed to contact a right palm and a left palm when said person wears said wearable body structure.

9. The apparatus of claim 1, wherein said pair of electrodes is formed to contact a right ankle and a left ankle when said person wears said wearable body structure.

10. The apparatus of claim 1, wherein said predetermined data includes height age, and sex of said person.

11. An apparatus for detecting a body-fat composition of a person, comprising:
   a pair of shoes having a weight sensor;
   a wearable body structure, of flexible material, having an inner surface;
   a flexible electrical conductor affixed to said inner surface, said conductor having a first-end portion and a second-end portion;
   an impedance-measuring circuit having at least one pair of electrodes, said pairs of electrodes being electrically coupled to said first end of said electrical conductor and said second end of said electrical conductor;
   a memory for storing data, which includes height, age, and sex of said person; and, a controller for processing data received from said weight sensor, said impedance-measuring circuit, and said memory to determine the body-fat composition of said person.

12. The apparatus of claim 11, further comprising a display for displaying the body-fat composition of said person.

13. The apparatus of claim 11, further comprising a power source for providing an electrical flow between said pair of electrodes.

14. The apparatus of claim 11, wherein said pair of electrodes is provided in said shoes for contact with a right sole and a left sole for measuring the impedance based on a voltage difference between said pair of electrodes.

15. The apparatus of claim 11, wherein said pair of electrodes is formed to contact a right palm and a left palm when said person wears said wearable body structure.

16. The apparatus of claim 11, wherein said pair of electrodes is formed to contact a right ankle and a left ankle when said person wears said wearable body structure.

17. The apparatus of claim 11, wherein said electrical conductor is integrated into the flexible material of said wearable body structure in the form of fibers of conductive material supported by fibers of substantially non-conductive material.

18. The apparatus of claim 11, wherein said electrical conductor is printed on said inner surface of said wearable body structure in the form of electrically conductive coating material.

19. A method for measuring the body-fat composition of a person, the method comprising the steps of:
   (a) inputting height, sex, and age of said person to a controller;
   (b) standing on a pair of shoes having a weight-measuring sensor to measure the weight of said person and to contact a right sole and a left sole on a pair of electrodes;
   (c) providing an electrical path between said pairs of electrodes;
   (d) detecting a voltage difference between said pair of electrodes to measure an impedance by means of an impedance-measuring circuit; and,
   (e) calculating a body-fat percentage by means of said controller.

20. The method of claim 18, further comprising the step of wearing a garment structure having a flexible electrical conductor coupled to a second pair of electrodes at both ends thereof, thereby making contact with a right wrist and a left wrist on said second pair of electrodes and repeating steps (c) through (e).

21. The method of claim 20, further comprising the step of displaying said body-fat percentage of said person.

* * * * *